United States Patent [19]
Slocum

[11] Patent Number: 5,752,953
[45] Date of Patent: May 19, 1998

[54] METHOD AND DEVICE FOR ADJUSTING A LONG-BONE CONFORMATION

[76] Inventor: Barclay Slocum, 34235 Van Duyn Rd., Eugene, Oreg. 97408

[21] Appl. No.: 791,287

[22] Filed: Jan. 30, 1997

[51] Int. Cl.⁶ ........................................... A61B 17/56
[52] U.S. Cl. ........................... 606/57; 606/58; 606/59
[58] Field of Search ........................... 606/59, 58, 57, 606/56, 55, 54, 87

[56] References Cited

U.S. PATENT DOCUMENTS 3,877,424  4/1975  Murray ................................. 606/54
4,677,973  7/1987  Slocum.

*Primary Examiner*—Michael Buiz
*Assistant Examiner*—Julian W. Woo
*Attorney, Agent, or Firm*—Kolisch, Hartwell, Dickinson, McCormack & Heuser

[57] ABSTRACT

An osteotomy procedure for adjusting the conformation of a long-bone is described. Illustratively, a proximal tibial osteotomy procedure produces two relatively rotatable long-bone segments. A jig including a body and having two pins extending therefrom in the same direction in a plane containing the long axis of the jig preferably is used to adjustably fix the two segments relative to one another with each pin securely fixed within a corresponding one of the segments. Importantly, at least the distal pin is bendable such that a desired rotation with two degrees of freedom is achievable between the two to-be-fixed segments. By bending the distal pin in a region thereof extending between the jig body and the distal segment, any desired relative rotation may be achieved between the segments. Correction of any and all conditions including varus, valgus, internal and external rotation may be accomplished in a single osteotomy procedure.

20 Claims, 1 Drawing Sheet

METHOD AND DEVICE FOR ADJUSTING A LONG-BONE CONFORMATION

TECHNICAL FIELD

The invention involves adjustment of an undesirable long-bone conformation, e.g. the conformation of a tibia, femur, radius/ulna or humerus, by relative rotation of two proximal osteotomy-produced long-bone segments. More specifically, it concerns adjustment using a jig having pins extending therethrough into such segments, whereby the distal pin is bent to produce a desired rotation of the distal segment that is pinned thereby. A preferred device and manner of practicing the invention is described in conjunction with veterinary surgery on the leg of a canine to correct an abnormal knee conformation.

BACKGROUND

A tibial plateau-leveling osteotomy procedure is known that permits adjustment of the axis of the tibia relative to that of the femur. Such a procedure is described in my U.S. Pat. No. 4,677,973 entitled PROXIMAL, TIBIAL OSTEOTOMY FOR LEVELING A TIBIAL PLATEAU, which issued Jul. 7, 1987. In accordance with that procedure, a through curvilinear cut is made in the proximal tibia to separate the metaphysis from a distal tibial segment. The axis of the curved cut is normal to the sagittal plane. The separated tibial segment is rotated a desired direction and angle about the knee joint. The relatively rotated metaphysis and distal tibial segment are then fixed relative to one another, as by pinning. The procedure may be used to solve such problems as cranial tibial thrust. The procedure described therein does not address varus, valgus, internal or external rotation of a long-bone segment.

SUMMARY OF THE INVENTION

Briefly, the invention involves a long-bone osteotomy procedure that produces two relatively rotatable bone segments separated by a transverse cut. A jig including a body and having two pins extending therefrom in the same direction in a plane containing the long axis of the jig preferably is used to adjustably fix the two segments relative to one another with each pin securely fixed within a corresponding one of the segments. Importantly, at least the distal pin is bendable such that a desired rotation with two degrees of freedom is achievable between the two to-be-fixed segments. By bending the distal pin in a region thereof extending between the jig body and the distal segment, any desired relative rotation may be achieved between the segments. Correction of any and all conditions including varus, valgus, internal and external rotation may be accomplished in a single osteotomy procedure.

These and additional objects and advantages of the present invention will be more readily understood after a consideration of the drawings and the detailed description of the preferred method.

DETAILED DESCRIPTION OF THE DRAWINGS AND BEST MODE FOR CARRYING OUT THE INVENTION

Figure 1:
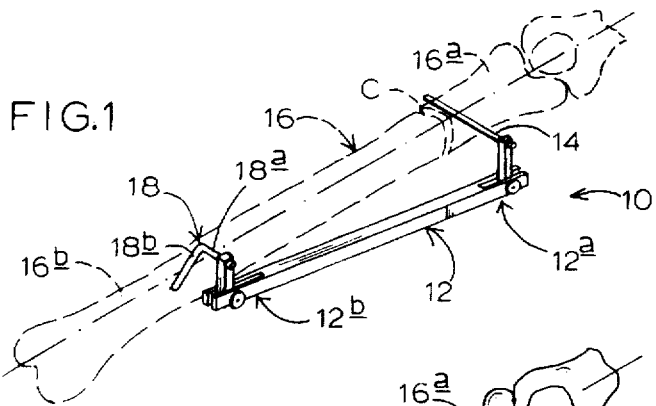
FIG. 1 is an isometric view of the invented jig made in accordance with its preferred embodiment, with a canine's tibia and distal femoral fragment shown in dashed outline.

Referring first to FIG. 1, an invented jig for imparting rotation or torsion or both between two cut and separated bone segments is shown at 10 in isometric view. Jig 10 may be seen in its preferred embodiment to include an elongate body 12 having a proximal articulable arm region 12a and a distal articulable arm region 12b; a first, elongate, substantially straight pin 14 extending substantially perpendicularly through proximal region 12a, with first pin 14 being configured for secure fixation within a proximal segment 16a of a bone such as a tibia 16; and a second, elongate, bent or angular pin 18 extending along a proximal extent thereof substantially perpendicularly through distal region 12b and substantially parallel with first pin 14, with second pin 18 extending along a distal extent 18b thereof at a predefined angle A relative to that of a proximal extent 18a and with second pin 18 being configured for secure fixation within distal segment 16b of the bone. Preferably, predefined angle A subtended between proximal extent 18a and distal extent 18b of second pin 18 is between approximately 135-degrees and 165-degrees, as shown in FIG. 1. (Those of skill in the art will appreciate that shown only fragmentarily in FIGS. 1 through 4 for the purpose of context are the humerus to which the tibia connects proximally and the ankle joint to which the tibia connects distally.)

It may be seen from FIGS. 1 through 4 that, in accordance with a preferred embodiment of the invention, proximal and distal regions 12a, 12b securely capture pins 14, 18 within opposite articulating arms that are pivotable, but securably so, within open slotted opposite end regions of body 12. This structure permits the articulable arms with their affixed pins to be oriented relative to body 12 through a wide range of angles that render apparatus 10 more conveniently manipulated relative to the osteotomy patient's long-bone. It will be appreciated that the articulable arms may be secured in a desired pivotal position relative to elongate body 12, e.g. the substantially perpendicular orientation shown in FIGS. 1 through 4, by the use for example of a set screw (illustrated in the drawings as being disk-shaped and Allen-wrench securable) in either end region.

Figure 5A:
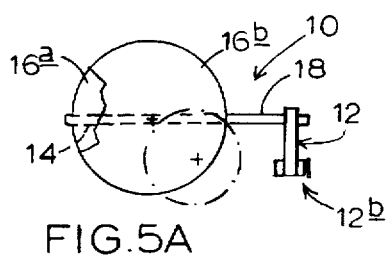
FIGS. 5A, 5B and 5C schematically illustrate the preferred invented method and jig, and show how the pin-bending step of the invented method effects both rotation and torsion of the distal tibial segment.
Figure 5B:
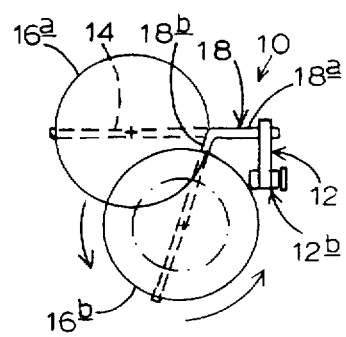
Figure 5C:
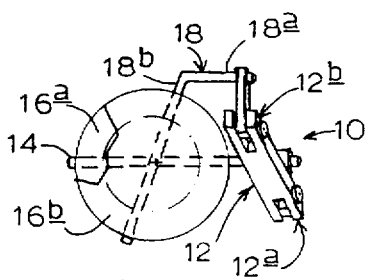

Those of skill in the art will appreciate that pins 14, 18 preferably are dimensioned to extend entirely through both cortices of the long-bone segments being adjusted, thereby to better secure the adjusted position of the bones, as illustrated best perhaps in FIGS. 5A through 5C. This is especially important when the long-bone being torsed or otherwise adjusted has a substantially hollow interior or void, as is typically the case with a proximal tibia. Those of skill also will appreciate that pins 14, 18 preferably extend through and slightly beyond the holes formed in the distal and proximal end regions of elongate body 12, as this facilitates gripping of the pins and further rotational adjustment thereof after the pins are secured within the long-bone segments.

Pins 14, 18 may be made of any suitable material and hardness. To some extent, pin size is patient limb size-dependent. Pin diameters range typically range from ⅛-inch to 3/32-inch, and pin lengths range typically from three to five inches. One suitable material, that has a desirable hardness and flexibility is 316L or 316LVM (low-carbon vacuum melt). The flexibility of the pins used in accordance with the invented jig is important in that it permits some flexing, to accommodate procedural tolerances, yet it has sufficient memory to maintain an imparted bend. Body 12 also may be made of any suitable material and may have two or more preferably parallel, and preferably perpendicular, holes formed in the arm regions 12a, 12b thereof through which pins 14, 18 may extend, and may be selectively slid axially or rotated around their axes, and yet may be captured, as by form-fitting them or by the use of a set screw (not shown). The slidable and rotatable but secure capture of pins 14, 18 within body 12 of apparatus 10 permits the body to be closer or further from the patient and for an optional step of torsing jig 10, as will be described by reference to FIGS. 4 and 5C.

The preferred method of the invention may be understood to achieve adjustment of the orientation of any distal bone relative to the proximal bone. For example, a distal tibia having an undesirable orientation or rotation may be adjusted by the invented method relative to the knee joint, or a distal femur having an undesirable orientation or rotation may be adjusted by the invented method relative to the hip joint. Those of skill in the art will appreciate that adjustment of any long-bone relative to a joint of which the long-bone is a part is within the spirit and scope of the invention, although the invented method is described and illustrated herein as involving a canine's proximal tibia and its associated knee joint.

Figure 2:
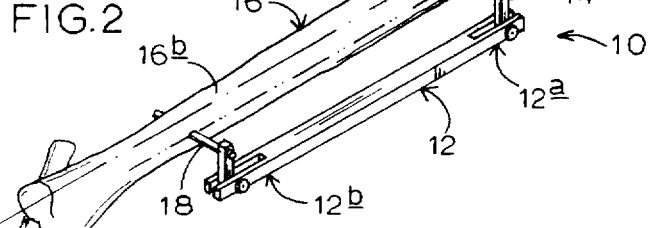
FIG. 2 is a fragmentary, isometric view of a cut-and-separated proximal tibia and knee joint of a canine, with the jig of FIG. 1 affixed thereto in accordance with an early and an intermediate step of the invented method.

Turning now to FIG. 2, it may be seen that the first step of the preferred method of the invention involves producing a transverse through cut C in a proximal region of bone 16 to produce separated proximal and distal bone segments, such as proximal tibial bone segment 16a and distal tibial bone segment 16b. Osteotomy cut C may be generally planar or generally cylindrical or otherwise curvilinear. If it is desired to achieve, intra-operatively, tibial plateau leveling, then it is preferred that the cut be cylindrical in accordance with the teachings of my above-referenced patent. It will be appreciated that, if no tibial plateau leveling is required, a simple planar cut will permit the needed tibial-knee joint adjustment. Any osteotomy cut that produces separated long-bone segments is contemplated, and is within the spirit and scope of the invention.

Referring still to FIG. 2, it may be seen that an intermediate step of the preferred method involves the use of jig 10 described above by reference to FIG. 1. Preferably, jig 10 is affixed to bone 16, with elongate proximal pin 14 extending therefrom into secure and preferably through engagement with proximal bone segment 16a and with elongate distal pin 18 extending therefrom into secure and preferably through engagement with distal bone segment 16b. It will be appreciated that by pin is meant any suitable temporary fixation device such as a pin or screw. Often, a distal region of such a pin is pointed and threaded for more secure engagement with the bone, although such is not required by the present invention.

Figure 3:
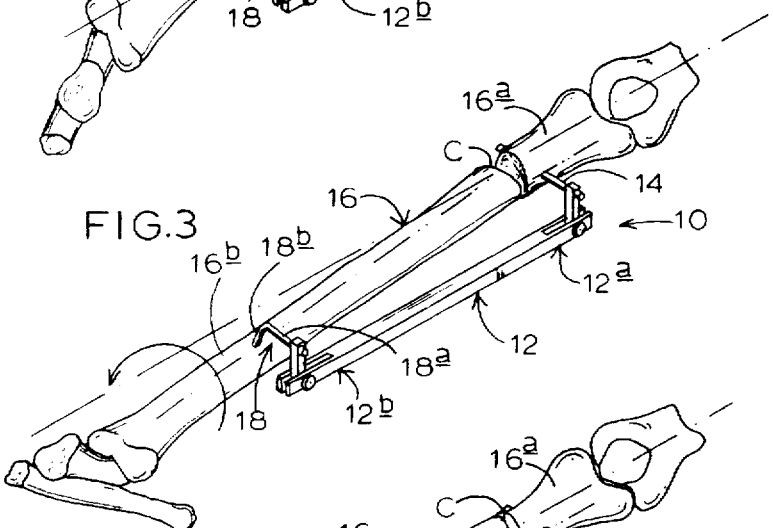
FIG. 3 is an isometric view corresponding with FIG. 2, but showing a later step in the invented method by which the jig's distal pin is bent into a predefined angular configuration to produce rotation and/or torsion of the distal tibia relative to the proximal tibia.

Turning now to FIG. 3, it may be seen that at least one of proximal pin 14 and distal pin 18 is bent, in accordance with a later step of the preferred method of the invention, in a region between body 12 of jig 10 and the engaged bone segment. Importantly, the bending step is performed after the affixing step in accordance with the preferred method of the invention, as it is the bending step that promotes rotation and/or torsion of the affected limb. Preferably, the bending is performed in a region of distal pin 18 that is approximately midway along the extent thereof between body 12 and bone 16. Nevertheless, those of skill in the art will appreciate that, alternatively yet within the spirit and scope of the invention, the pin may be bent closer to the body or closer to the bone, as access and pin length permit, and that proximal pin 14 may be bent instead or in addition to the bending of distal pin 18, thereby to promote desired rotation of distal bone segment 16b relative to proximal bone segment 16a.

It may be seen from FIG. 3 that the bending step produces an obtuse angular orientation between first, proximal extent 18a of distal pin 18 that is proximate jig 10 and a second, distal extent 18b of distal pin 18 that is in engagement with distal bone segment 16b. Preferably, the bending step produces an angular orientation of between approximately 145-degrees and 175-degrees, depending upon the desired degree of imparted rotation and torque, which range of angles has been found to be useful in correcting tibial and femoral conformations. More preferably, the bending step produces an angular orientation of approximately 165-degrees, as 15-degrees (180-degrees minus 165-degrees) is a more typical extent of correction required and as 15-degrees is the amount of correction that is imparted by forming an angle subtended between the first and second extents of the pin at approximately 165-degrees.

The most extreme undesirable conformations may require as much as approximately 35-degrees, or more, of correction, corresponding to a subtended angle of approximately 145-degrees. Slight undesirable conformations may require as little as approximately 5-degrees of correction, corresponding to a subtended angle of approximately 175-degrees. Thus, those of skill will appreciate that the bending step may be performed in such manner that any desired angle is subtended by first and second distal pin extents 18a, 18b. This is one of the excellent advantages of the invention: any desired angle is easily achieved by the claimed bending of a pin into a desired angular configuration.

Figure 6:
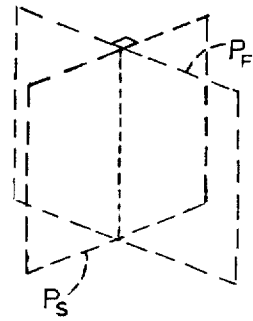
FIG. 6 is a schematic diagram of the various anatomical planes that, relative to FIGS. 1 through 4, help define certain angular adjustments and resulting orientations disclosed herein.

It may be seen from FIG. 3 that the bending step preferably is performed in such manner that first and second extents 18a, 18b of distal pin 18 define a plane $P_p$ (refer briefly to FIG. 5B, the plane of which corresponds with this plane $P_p$), which intersects the patient's sagittal plane $P_s$ (a vertical plane normal to that of FIG. 5B, and one shown in FIG. 6). It also may be seen from FIG. 3 that the bending step preferably is performed in such manner that first and second extents 18a, 18b of distal pin 18 define a plane that also intersects the patient's frontal plane $P_F$ (a plane normal to sagittal plane $P_S$, i.e. a plane that it is parallel with the plane of FIG. 5B, and one shown in FIG. 6, described below). Those of skill in the art will appreciate that one or both intersections may be effected simultaneously by the manner in which the bending step of the invented method is performed. This is another excellent advantage of the invention over prior art jigs that permit rotation of a pin only about the jig's long axis or in a plane parallel to a plane containing the jig's long axis.

Those of skill will appreciate that, because the pins of jig 10 are securely attached to the distal and proximal long-bone segments and are securely fixed within jig 10, the bending of distal pin 18 results in the commensurate torsing of distal segment 16b relative proximal segment 16a (refer to FIG. 3 in which such torsing, or relative rotation, is illustrated schematically by a curved arrow). It may also be seen from FIG. 3 that such bending step produces an incidental angular adjustment of the distal end of long-bone 16 (refer again to FIG. 3 in which such incidental angular adjustment is illustrated schematically by non-coaxial, or intersecting, dash-dot and dash-dot-dot lines corresponding, respectively, with the central axis of segment 16a and segment 16b)

Figure 4:
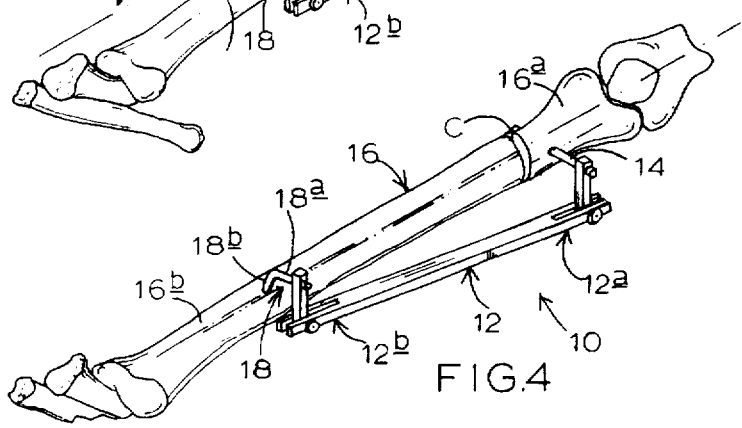
FIG. 4 is an isometric view corresponding with FIG. 3, but showing a final step in the invented method by which the jig itself is rotated to produce the desired final long-bone configuration.

FIG. 4 may be seen to be similar to FIG. 3, but shows a further, optional, step in the preferred method of adjusting a long-bone conformation. In FIG. 4, jig 10 has been rotated generally clockwise (relative approximately to the plane of the drawings) through a defined angle with the pins securely fixed within the long-bone segments. The result of such jig rotation is the restoration of the coaxial orientation of segments 16a, 16b to compensate for the slight downward shift that resulted, as illustrated in FIG. 3, from the bending of pin 18 to cause rotational adjustment between the long-bone segments. This rotation of jig 12 is illustrated schematically in FIG. 5C to be described below.

Not shown in FIG. 4 is a step that forms no part of the present invention by which fixation of the adjusted long-bone segments is accomplished, as by any suitable method including internal or external fixation devices such as pins, brackets, etc. Also not shown in FIG. 4 is a final step in the preferred osteotomy whereby any needed bone grafting is performed in and around the interface between the adjusted long-bone segments. Such will be understood by those skilled in the art to promote better fixation and faster osteosynthesis, especially in a case where—by the nature of the transverse cut or the resulting configuration between the cut, separated, adjusted and fixated segments—there is a bone material deficit.

FIGS. 5A through 5C schematically illustrate in an axial view along the tibia the tibial configuration before and after the pin-bending step and after the jig-torsing step. Briefly, FIG. 5A represents tibia 16 by its two cut and separated segments 16a and 16b shown as concentric circles, with an intermediate portion thereof shown in dash-dot outline as a smaller circle that is not concentric with the others. FIG. 5B shows that, with the bending of pin 18 of jig 12 as described and illustrated herein, distal tibial segment 16b may be shifted and rotated (as indicated by two curved arrows) relative to proximal tibial segment 16a, whereby a canine's hock joint is rotated internally or externally to correct a torsed condition of the tibia and whereby simultaneously the distal tibial segment is reoriented relative to the proximal tibial segment and the knee joint to correct a varus (knock-kneed) or valgus (bowlegged) condition of the canine's rear leg. Finally, FIG. 5C shows a final configuration of proximal and distal tibial segments 16a, 16b corresponding with that of FIG. 4 in which, by torsing jig 10 while pins 14, 18 are securely fixed in their respective long-bone segments, the distal and tibial segments are restored to a condition of being substantially coaxial, but with the imparted torsional adjustment therebetween.

If it is desired or needed to level the patient's tibial plateau, while also performing the rotational and/or torsional adjustment described and illustrated herein, then a curvilinear cut is produced in the proximal metaphysis of the patient's tibia, with the lower part of the cut being concave as viewed from the metaphysis. The cut is made generally perpendicular to the sagittal plane, thereby freeing a caudal, tibial portion within the metaphyseal region of the tibia for movement relative to the remaining portion of the tibia that includes the diaphysis of the tibia and the tibial crest. In this case, the invented bending step produces a tibial plateau leveling, as described in my referenced patent, as well as rotation of the thus-cut-separated tibial portions to produce a new fixed angular relationship therebetween.

Briefly referring now to FIG. 6, which will be understood to be oriented consistent with the isometric views of FIGS. 1 through 4, the anatomical planes are illustrated schematically as dash-outlined rectangles labeled $P_S$ (representing the patient's sagittal plane) and $P_F$ (representing the patient's frontal plane) intersecting one another normally, or at a right angle, in a line of intersection indicated in FIG. 6 by a dotted line. These planes are believed to be well understood by those of skill in the art, and are included for the sake of completeness and clarity.

Accordingly, while a preferred embodiment of the invention has been described herein, and preferred methods associated therewith, it is appreciated that modifications are possible that are within the scope of the invention.

I claim:

1. A method for adjusting the orientation of a distal bone relative to a proximal joint of which it is a part, the method comprising the steps of:
   producing a through cut in a proximal region of the bone to produce separated proximal and distal bone segments;
   affixing to the bone a jig including a body, an elongate proximal pin extending therefrom into secure engagement with the proximal bone segment, and an elongate distal pin extending therefrom into secure engagement with the distal bone segment; and
   bending at least one of the affixed pins in a region between the body and the engaged bone segment thereby to promote rotation of the distal bone segment relative to the proximal bone segment.

2. The method of claim 1, wherein said bending produces an obtuse angular orientation between a first extent of the distal pin that is proximate the jig and a second extent of the distal pin that is in engagement with the distal bone segment.

3. The method of claim 2, wherein said bending produces such an angular orientation between approximately 145-degrees and 175-degrees.

4. The method of claim 2, wherein said bending step is performed in such manner that the first and second extents of the distal pin define a plane that intersects the sagittal plane.

5. The method of claim 2, wherein said bending step is performed in such manner that the first and second extents of the distal pin define a plane that intersects the frontal plane.

6. The method of claim 2, wherein said bending step is performed in such manner that the first and second extents of the distal pin define a plane that intersects the sagittal plane and the frontal plane.

7. The method of claim 6, wherein said bending produces an obtuse angular orientation between a first extent of the distal pin that is part of the jig and a second extent of the distal pin that is in engagement with the distal bone segment, and wherein such angular orientation is between approximately 145-degrees and 175-degrees.

8. The method of claim 1, wherein said producing is of a curvilinear cut.

9. The method of claim 1, wherein said producing is of a generally cylindrical cut.

10. The method of claim 1 in which the bone is a tibia, wherein said producing is of a curvilinear cut adjacent the proximal metaphysis of the tibia, the lower part of which cut is concave as viewed from such metaphysis, such cut being made generally perpendicular to the sagittal plane, to free a caudal, tibial portion within the metaphyseal region of the tibia for movement relative to the remaining portion of the tibia that includes the diaphysis of the tibia and the tibial crest, wherein bending produces a rotation of the thus-cut-separated tibial portions to produce a new fixed angular relationship therebetween.

11. A jig for imparting rotation or torsion or both between two cut and separated bone segments, the jig comprising:

an elongate body having a proximal region and a distal region;

a first substantially straight pin extending substantially perpendicularly from said proximal region of said body, said first pin being configured for secure fixation within the proximal segment of the bone; and a second angular pin with a proximal extent thereof extending substantially perpendicularly from said distal region of said body, said second pin pivotable and securable with respect to said body, said pin with a distal extent thereof extending at a predefined angle relative of that of said proximal extent, said second pin being configured for secure fixation within the distal segment of the bone.

12. The jig of claim 11, wherein said predefined angle subtended between said proximal and said distal extents of said second pin is between approximately 145-degrees and 175-degrees.

13. The jig of claim 11, wherein said second pin is longitudinally adjustable with respect to said body.

14. The jig of claim 11, wherein said second pin comprises an articulable arm.

15. The jig of claim 14, wherein said body has a slotted distal end, and said articulable arm is securable within said slotted distal end.

16. The jig of claim 11, wherein said first pin is pivotable and securable with respect to said body.

17. The jig of claim 16, wherein said first and second pins are longitudinally adjustable with respect to said body.

18. The jig of claim 16, wherein said first pin comprises a first articulable arm and said second pin comprises a second articulable arm.

19. The jig of claim 18, wherein said body has a slotted proximal end and a slotted distal end.

20. The jig of claim 19, wherein said first articulable arm is securable within said slotted proximal end and said second articulable arm is securable within said slotted distal end.

* * * * *